US006673964B1

(12) United States Patent
Uriarte et al.

(10) Patent No.: US 6,673,964 B1
(45) Date of Patent: Jan. 6, 2004

(54) PROCESS FOR PRODUCING A CALCIUM CARBOXYLATE

(75) Inventors: Anthony K. Uriarte, Pensacola, FL (US); Norman J. Peters, Pensacola, FL (US); Mikhail I. Khramov, Pensacola, FL (US); Thomas W. Backes, Pace, FL (US); Patrick N. Crowe, Pensacola, FL (US); Deanna W. Hamilton, Gulf Breeze, FL (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 10/209,430

(22) Filed: Jul. 30, 2002

Related U.S. Application Data

(60) Provisional application No. 60/392,323, filed on Jun. 27, 2002.

(51) Int. Cl.$^7$ .......................... C07B 53/00; C07C 51/08
(52) U.S. Cl. ...................................... 562/606; 562/484
(58) Field of Search ................................. 562/606, 484

(56) References Cited

U.S. PATENT DOCUMENTS

| | | | |
|---|---|---|---|
| 3,876,691 | A | 4/1975 | Lincoln |
| 3,966,803 | A | 6/1976 | Vogt et al. |
| 4,700,000 | A | 10/1987 | Merkel et al. |
| 5,591,878 | A | 1/1997 | Nelson et al. |
| 5,707,679 | A | 1/1998 | Nelson |
| 5,763,652 | A | 6/1998 | Kawabe et al. |
| 5,795,615 | A | 8/1998 | Nelson et al. |
| 6,100,427 | A | 8/2000 | Bezuidenhout et al. |

*Primary Examiner*—Johann Richter
*Assistant Examiner*—Paul A. Zucker
(74) *Attorney, Agent, or Firm*—Banner & Witcoff Ltd.; John P. Foryt, Esq.

(57) ABSTRACT

A process for producing a calcium carboxylate comprising contacting a nitrile compound, a calcium compound selected from calcium hydroxide, calcium oxide or mixtures thereof, and water at a temperature of about 90° C. to about 250° C. at a sufficient pressure and for a sufficient time to produce a reaction mixture comprising calcium carboxylate.

40 Claims, No Drawings

PROCESS FOR PRODUCING A CALCIUM CARBOXYLATE

RELATED APPLICATIONS

This application claims priority of the prior provisional application Ser. No. 60/392,323, entitled "Process For Producing A Calcium Carboxylate" filed Jun. 27, 2002 which is hereby incorporated by reference into this application.

BACKGROUND OF THE INVENTION

This invention relates to a process for producing a calcium carboxylate from a nitrile compound using calcium hydroxide or calcium oxide and water. In one aspect, this invention relates to a process for producing calcium propionate from propionitrile and calcium hydroxide or calcium oxide.

Calcium carboxylates produced according to the process of the invention can be used to produce the corresponding carboxylic acids. Calcium carboxylates also have other uses. For example, calcium acetate is used as a thickening agent, such as in cake batters, puddings, and pie fillings, as buffers in controlling pH of food during various stages of processing as well as in the finished product, as a preservative to prevent microbial growth, and as a calcium supplement in pet products. In addition, calcium propionate is used on a large scale as a preservative in the foodstuffs sector, particularly in baked goods to inhibit molds and other microorganisms, and as a preservative and nutritional supplement in animal feeds.

Calcium carboxylates are typically prepared by the conventional methods for synthesizing carboxylic acid salts, for example by reacting a carbonate, hydroxide, or oxide with a concentrated or dilute carboxylic acid. Calcium propionate is typically produced from propionic acid and calcium hydroxide.

U.S. Pat. No. 4,700,000 (Merkel et al.) discloses an improvement to the conventional process for producing calcium propionate from propionic acid. Merkel et al. discloses that water formed during the reaction of calcium hydroxide with propionic acid is removed as an azeotropic mixture of water and propionic acid. Merkel et al. discloses that the vaporous mixture of water and propionic acid advantageously used for the preparation of calcium propionate by a process whereby this mixture is passed into an aqueous mixture containing calcium propionate and calcium hydroxide, with or without propionic acid, during which the pH is adjusted to 5–10 by further addition of calcium hydroxide, and the calcium propionate is isolated by crystallization.

U.S. Pat. No. 3,876,691 (Lincoln) discloses the hydrolysis of nitriles with an aqueous solution of barium hydroxide to produce the barium salt of the carboxylic acid corresponding to the nitrile. Lincoln, however, discloses that calcium oxide was ineffective as the hydrolyzing agent and that barium hydroxide is unique in its ability to hydrolyze nitriles as compared with the other most common alkaline earth metal hydroxide, i.e. calcium hydroxide (see Example III of Lincoln).

U.S. Pat. No. 5,763,652 (Kawabe et al.) discloses the hydrolysis of a nitrile compound with a basic catalyst to form a salt of a carboxylic acid and a base, wherein the basic catalyst is particularly an alkali metal hydroxide (col. 3, lines 4–6). Kawabe et al. also discloses the hydration of a nitrile compound to the corresponding amide in the presence of a manganese oxide catalyst. Optionally, the hydration of the nitrile compound can be conducted in the presence of a combination of the manganese oxide and a metallic simple substance or compound containing Group Ia elements (e.g. Na, K, etc.), Group IIa elements (e.g. Mg, Ca, Ba, etc.), Group IIb elements (e.g. Zn), Group IVa elements (e.g. Zr, etc.), Group IVb elements (e.g. Sn, etc.), and Group Va elements (e.g. V, etc.). (See col. 12, lines 26–65). Kawabe et al. further discloses that the amide compound formed by the hydration of the nitrile compound can be hydrolyzed by an inorganic base, for example, alkali metal hydroxides, alkali metal carbonates, alkali metal hydrogencarbonates, alkaline earth metal hydroxides, and alkali earth metal carbonates, preferably alkali metal hydroxides and carbonates (see col. 15, lines 47–57, and col. 16, lines 1–6). Kawabe et al. does not disclose the hydrolysis of a nitrile compound with calcium hydroxide nor the hydration of a nitrile compound with a calcium compound alone.

Therefore, to produce calcium propionate from propionitrile, one of ordinary skill in the art would first convert the propionitrile to the free acid via acid or caustic hydrolysis. The acid hydrolysis would produce large amounts of a byproduct ammonium salt. Typical base hydrolysis with caustic soda, i.e. sodium hydroxide, would consume large quantities of sodium hydroxide, or require capital-intensive electrodialysis to recover the sodium hydroxide. The acid would subsequently be reacted with calcium hydroxide or calcium oxide to produce calcium propionate. In the alternative, one of ordinary skill in the art, based on the teaching of the Kawabe et al. patent, would hydrate a nitrile compound using a manganese oxide catalyst to produce the corresponding amide and then hydrolyze the amide compound using a base, e.g. calcium hydroxide.

A commercially practical process for producing calcium carboxylates directly from nitrile compounds and a calcium compound has now been discovered.

SUMMARY OF THE INVENTION

According to the invention, a process for producing a calcium carboxylate is provided comprising contacting a nitrile compound, a calcium compound selected from calcium hydroxide, calcium oxide or mixtures thereof, and water at a temperature of about 90° C. to about 250° C. at a sufficient pressure and for a sufficient time to produce a reaction mixture comprising calcium carboxylate.

Further according to the invention, ammonia is removed from the reaction mixture and the calcium carboxylate is recovered.

Still further according to the invention, a process for producing a calcium carboxylate is provided comprising (a) contacting a nitrile compound, a calcium compound selected from calcium hydroxide, calcium oxide or mixtures thereof, and water in a reaction vessel at a temperature of about 90° C. to about 250° C. at a sufficient pressure and for a sufficient time to produce a first reaction mixture comprising calcium carboxylate, the amide corresponding to the nitrile compound, calcium hydroxide, water and ammonia; (b) venting the reaction vessel with or without prior cooling to remove ammonia and produce a second reaction mixture; (c) optionally adding additional water to the second reaction mixture; (d) heating the second reaction mixture to a suitable temperature to remove additional ammonia and, optionally, water from the second reaction mixture and hydrolyze at least a portion of the amide to produce additional calcium carboxylate; and (e) recovering the calcium carboxylate.

BRIEF DESCRIPTION OF THE DRAWINGS

NOT APPLICABLE.

DETAILED DESCRIPTION OF THE INVENTION

This invention provides a process for producing calcium carboxylate directly from a nitrile compound using a calcium compound selected from calcium hydroxide, calcium oxide and mixtures thereof, with the proviso that the hydrolysis of the nitrile compound with the calcium compound can be conducted without the presence of a separate catalyst, such as a manganese oxide catalyst.

A first embodiment of the invention relates to a process for producing a calcium carboxylate comprising contacting a nitrile compound, a calcium compound selected from calcium hydroxide, calcium oxide or mixtures thereof, and water at a temperature of about 90° C. to about 250° C. at a sufficient pressure, i.e. a pressure sufficient to achieve the desired temperature, and for a sufficient time to produce a reaction mixture comprising calcium carboxylate.

After formation of the reaction mixture comprising calcium carboxylate, the reaction mixture is typically further processed to remove ammonia from the reaction mixture and the calcium carboxylate is recovered.

A second embodiment of the invention relates to a preferred process for producing a calcium carboxylate comprising (a) contacting a nitrile compound, a calcium compound selected from calcium hydroxide, calcium oxide or mixtures thereof, and water in a reaction vessel at a temperature of about 90° C. to about 250° C. at a sufficient pressure, i.e. a pressure sufficient to achieve the desired temperature, and for a sufficient time to produce a first reaction mixture comprising calcium carboxylate, the amide corresponding to the nitrile compound, calcium hydroxide, water and ammonia; (b) optionally cooling the first reaction mixture, (c) venting the reaction vessel to remove ammonia and produce a second reaction mixture; (d) optionally adding additional water to the second reaction mixture; (e) heating the second reaction mixture to a suitable temperature to remove additional ammonia and, optionally, water from the second reaction mixture and hydrolyze at least a portion of the amide to produce additional calcium carboxylate; and (f) recovering the calcium carboxylate.

Nitrile compounds that can be employed according to the invention include nitrile compounds represented by the formula R—CN, wherein R is selected from an aliphatic hydrocarbon group, an alicyclic hydrocarbon group, an aromatic hydrocarbon group, or a heterocyclic hydrocarbon group, and wherein R is optionally substituted.

The aliphatic hydrocarbon group includes, but is not limited to, saturated hydrocarbon groups having about 1 to 12 carbon atoms, preferably about 1 to 6 carbon atoms, or unsaturated hydrocarbon groups having about 2 to 12 carbon atoms, preferably about 2 to 6 carbon atoms. Examples of suitable saturated aliphatic hydrocarbon groups include methyl, ethyl, propyl, isopropyl, butyl, isobutyl, s-butyl, t-butyl, pentyl, hexyl, octyl, decyl, and the like. Examples of suitable unsaturated aliphatic hydrocarbon groups includes vinyl, allyl, 1-propenyl, isopropenyl, 2-butenyl, ethynyl, 2-propynyl, and the like.

The alicyclic hydrocarbon group includes, but is not limited to, cycloalkyl and cycloalkene groups having about 3 to 10 carbon atoms. Examples of suitable alicyclic hydrocarbon groups include cyclopropyl, cyclobutyl, cyclopentyl, cyclohexyl, cyclooctyl, and cycloalkylene groups corresponding to these cycloalkyl groups.

The aromatic hydrocarbon group includes, but is not limited to, aryl groups having about 6 to 14 carbon atoms, and alkaryl and aralkyl groups having about 7 to 15 carbon atoms. Examples of suitable aromatic hydrocarbon groups include phenyl, naphthyl, benzyl, phenethyl, tolyl, xylyl, and the like.

The heterocyclic group includes heterocyclic groups each having at least one atom, as a hetero atom, selected from a nitrogen atom, an oxygen atom, or a sulfur atom, and may be whichever of an aromatic heterocyclic group, a non-aromatic heterocyclic group, or a condensed heterocyclic group. Examples of suitable heterocyclic groups include furyl, thienyl, pyrrolyl, imidazolyl, pyrrolidinyl, pyridyl, pyrazinyl, pyrimidinyl, indolyl, pyridazinyl, piperidino, morpholino, morpholinyl, quinolyl, and the like.

These groups represented by R may optionally be substituted. Examples of suitable substituents include halogen atoms, a hydroxyl group, alkyl groups (e.g. methyl, ethyl, propyl, isopropyl and other $C_{1-5}$ alkyl groups), aryl groups (e.g. phenyl, tolyl, xylyl, chlorophenyl, methoxyphenyl, naphthyl and other $C_{6-14}$ aryl groups), ether groups, alkoxy groups (e.g. methoxy, ethoxy and other $C_{1-5}$ alkoxy groups), aryloxy groups (e.g. phenoxy and other $C_{6-14}$ aryloxy groups), a mercapto group, alkylthio groups (e.g. methylthio, ethylthio and other $C_{1-5}$ alkylthio groups), arylthio groups (e.g. phenylthio and other $C_{6-14}$ arylthio groups), a carboxyl group, ester groups (e.g. methoxycarbonyl and other $C_{1-6}$ alkoxy-carbonyl groups); acetoxy and other $C_{2-12}$ acyloxy groups, acyl groups (e.g. acetyl, benzoyl and other $C_{2-12}$ acyl groups), amino groups, including mono- or di-substituted amino groups (e.g. methylamino, dimethylamino and other mono- or di-$C_{1-5}$ alkylamino groups), a nitro group, and the like. The number of such substituents to be substituted on the R group represented may be about 1 to 4.

Examples of suitable aliphatic nitriles include acetonitrile, propionitrile, butyronitrile, isobutyronitrile, valeronitrile, isovaleronitrile, capronitrile and other saturated mononitriles; malononitrile, succinonitrile, glutaronitrile, adiponitrile, α-aminopropionitrile, α-aminomethylthiobutyronitrile, α-aminobutyronitrile, aminoacetonitrile; lactonitrile, hydroxyacetonitrile, α-hydroxyisobutyronitrile (acetocyanohydrin), α-hydroxy-γ-methylthiobutyronitrile (4-methylthio-2-hydroxybutyronitrile); cyanoacetic acid; amino-3-propionitrile, and unsaturated nitriles (e.g. acrylonitrile, methacrylonitrile, allyl cyanide, crotononitrile), and the like.

Examples of suitable alicyclic nitriles include cyclopentanecarbonitrile, cyclohexanecarbonitrile, and the like.

Examples of suitable aromatic nitriles include benzonitrile, o-, m- and p-chlorobenzonitrile, o-, m- and p-fluorobenzonitrile, o-, m- and p-nitrobenzonitrile, p-aminobenzonitrile, 4-cyanophenol, o-, m- and p-tolunitrile, 2,4-dichlorobenzonitrile, 2,6-dichlorobenzonitrile, 2,6-difluorobenzonitrile, anisonitrile, α-naphthonitrile, β-naphthonitrile, phthalonitrile, isophthalonitrile, terephthalonitrile, benzyl cyanide, cinnamoyl nitrile, phenylacetonitrile, mandelonitrile, p-hydroxyphenylacetonitrile, p-hydroxyphenylpropionitrile, p-methoxyphenylacetonitrile and the like.

Examples of suitable heterocyclic nitriles include nitrile compounds each having a heterocyclic group containing 5- or 6-membered ring and having at least one atom selected from a nitrogen atom, an oxygen atom or a sulfur atom as a hetero atom, such as 2-thiophenecarbonitrile, 2-furonitrile, 2-cyanopyridine, 3-cyanopyridine, 4-cyanopyridine, cyanopyrazine, 5-cyanoindole, cyanopiperidine, cyanopiperazine, and the like.

More particularly, the nitrile compound in which the aliphatic hydrocarbon group, alicyclic hydrocarbon group, aromatic hydrocarbon group or heterocyclic group represented by R has a substituent, includes amino-nitrile compounds, cyanohydrin compounds and the like. Examples of the aminonitrile compounds include aminoacetonitrile, α-aminopropionitrile, α-aminobutyronitrile, 3-aminopropionitrile, and the like. Examples of the cyanohydrin compounds include α-cyanohydrin compounds, ,β-cyanohydrin compounds, γ-cyanohydrin compounds and the like. Such cyanohydrin compound may contain, for instance, about 2 to 18, preferably about 3 to 12, and more preferably about 3 to 8 carbon atoms.

The suitable α-cyanohydrin compounds can be represented by the formula

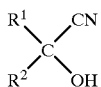

wherein $R^1$ and $R^2$ independently represent a hydrogen atom or a hydrocarbon group which may have a substituent, and $R^1$ and $R^2$ may form a ring together with the adjacent carbon atom, with a proviso that $R^1$ and $R^2$ are not concurrently hydrogen atoms.

Examples of the hydrocarbon group represented by $R^1$, $R^2$, and the substituent which the hydrocarbon group may have include the aliphatic hydrocarbon groups, alicyclic hydrocarbon group, aromatic hydrocarbon group, and the substituents which these groups may have, as described above for the group R.

Examples of the ring which is formed with $R^1$ and $R^2$ together with the adjacent carbon atom include cyclopropyl, cyclobutyl, cyclopentyl, cyclohexyl, cycloheptyl, cyclooctyl, and the like.

Examples of suitable α-cyanohydrin compound include hydroxyacetonitrile, lactonitrile, acetone cyanohydrin, 2-hydroxybutanenitrile, 2-hydroxy-4-methylthiobutanenitrile, 2-hydroxy-2-methylbutanenitrile, 2-hydroxy-3-methylbutanenitrile, 2-hydroxy-3-butenenitrile, 2-hydroxypentanenitrile, 2-hydroxyhexanenitrile, 2-hydroxyoctanenitrile and other aliphatic .alpha.-cyanohydrins; 2-hydroxycyclohexaneacetonitrile, cyclopentanone cyanohydrin, cyclohexanone cyanohydrin, mandelonitrile, 2-hydroxy-3-phenylbutanenitrile, and the like.

Examples of suitable β-cyanohydrin compounds include 3-hydroxypropanenitrile, 3-hydroxybutanenitrile, 3-hydroxyhexanenitrile, 2-hydroxycyclohexanecarbonitrile or 3-hydroxy-3-phenylpropanenitrile.

Examples of suitable γ-cyanohydrin compounds includes 4-hydroxy-butanenitrile, 4-hydroxyhexanenitrile, 3-hydroxyhexanecarbonitrile, 4-hydroxy-4-phenylbutanenitrile, and the like.

The nitrile compound is preferably a compound where the salt of the corresponding carboxylic acid is water-soluble. The currently preferred nitrile is propionitrile, which can be obtained as a byproduct of the adiponitrile manufacturing process, with the preferred calcium carboxylate being calcium propionate.

The nitrile compounds described above can be prepared by any conventional process known to those of skill in the art. For example, an aliphatic nitrile may be prepared by reacting an alkyl halide with sodium cyanide or other alkali metal cyanide. The aromatic nitrites can be produced by, for instance, a process comprising diazotizing an amine and allowing the resultant product to react with copper (I) cyanide, or other routes. Benzonitrile, for example, can be produced by reacting benzoic acid with urea in the presence of a metallic catalyst. The α-cyanohydrin compounds among such nitrile compounds may be prepared by, for example, a process which comprises allowing cyanide to react with an aldehyde or a ketone, a process which comprises allowing an adduct derived from an aldehyde or ketone and sodium hydrogen sulfite to react with an alkali cyanide such as potassium cyanide, or others. The β-cyanohydrin compound can be prepared by allowing an epoxide to react with hydrogen cyanide, for example.

Calcium compounds that can be employed according to the process of the invention are selected from calcium hydroxide, calcium oxide, or mixtures thereof. When calcium oxide is used, the conditions of the process will result in at least part of the calcium oxide being hydrolyzed to calcium hydroxide.

The amount of calcium compound employed in the process of the invention can conveniently be expressed as a molar ratio of calcium compound to nitrile compound charged to the reaction vessel. Broadly, the molar ratio of calcium compound to nitrile compound is about 0.5:1 to about 0.75:1. It is preferred to use a stoichiometric excess of calcium compound compared to the nitrile compound, i.e. a molar ratio greater than 0.5:1 will result in an excess of the calcium compound. For example a molar ratio of 0.75:1 corresponds to a molar excess of 50%. The molar ratio of calcium compound to nitrile compound is preferably greater than 0.5:1 to about 0.6:1 (an excess of calcium compound up to about a 20% molar excess), and most preferably about 0.505:1 to about 0.55:1 (a molar excess of about 1% to 10%).

The amount of water employed in the process of the invention is that amount necessary to conduct the process, e.g. water needed for the hydrolysis plus water to function as the reaction solvent/diluent. The amount of water employed in the process of the invention can conveniently be expressed as a molar ratio of water to nitrile compound charged to the reaction vessel. The molar ratio of water to nitrile compound is about 5:1 to about 30:1, preferably about 8:1 to about 18:1, and more preferably about 12:1 to about 15:1.

In cases where the nitrile compound is not sufficiently soluble in water, a co-solvent can be used to increase the solubility of the nitrile compound and improve process operation. Suitable co-solvents include Water-soluble organic solvents such as acetone and other ketones; methanol, ethanol and other alcohols; and ethylene glycol, glycerol and other polyols, dimethyl ether, tetrahydrofuran, dioxane and other ethers. Polyols can also aid the reaction by increasing the solubility of calcium hydroxide. The process of the invention can generally be conducted at a reaction temperature of about 90° C. to about 250° C., preferably about 120° C. to about 250° C., and more preferably about 160° C. to about 220° C. The process of the invention can be conducted at any suitable pressure depending on the desired reaction temperature and the method used for removal of ammonia from the reaction mixture. It is currently preferred to conduct the reaction at a pressure at or above the autogenic pressure based on the reaction temperature in order to maintain most of the water and the nitrile compound in the liquid phase. Such pressure will be readily apparent to one of ordinary skill in the art without undue experimentation. For example, when propionitrile is used as the nitrile compound and the reaction temperature is 170° C., the autogenic pressure is about 110–120 psia (about 758.4–827.4 KPa). If ammonia is to be removed during the reaction, such as continuously during the formation of the calcium carboxylate, the pressure is preferably at or above the autogenic pressure but a pressure below the autogenic pressure may be used. If a pressure below the autogenic pressure is used, it is preferred to recover and recycle any nitrile compound removed with the ammonia for optimum operation of the process of the invention. The reaction time will be the time suitable to obtain the desired conversion of the nitrile compound into calcium carboxylate. Generally, the reaction time will vary depending on process parameters including the reaction temperature and the nitrile used. The process of the invention can be conducted as a batch, semi-batch, or continuous process depending on the scale of the process and capital investment required.

After completion of the initial reaction whereby the reaction mixture comprising the calcium carboxylate is obtained, the process further comprises recovering and producing a calcium carboxylate product suitable for commercial use. As part of the recovery process, it will be necessary to remove ammonia if sufficient ammonia has not been removed during the reaction, i.e. production of the first reaction mixture.

Ammonia removal can be conducted by any conventional method known to those of ordinary skill in the art. One option for ammonia removal is to vent the reaction vessel vapor space following completion of the formation of the first reaction mixture. Depending on the temperature and pressure of the first reaction, this venting procedure would typically be expected to remove the majority, i.e. 55–95%, of the free ammonia. A second option is to cool the first reaction mixture to a temperature below the atmospheric boiling point, typically less than 70° C., prior to venting the headspace of the reaction vessel. This option is preferred if the configuration of the equipment used for the first reaction is not suitable for ammonia removal. After the venting process is completed, the remaining ammonia can be removed by heating the second reaction mixture at the pressure after the venting step, i.e. preferably at or near atmospheric pressure, to distill the ammonia overhead. The temperature that the second reaction mixture is heated to will be any suitable temperature effective to remove the desired amount of ammonia and will be readily apparent to those of ordinary skill in the art. Typically, the temperature is about 70° C. to about 105° C. If a straight takeover distillation is used, i.e. no rectification of the distillate, it may be necessary to boil a significant amount of water overhead to remove the ammonia to very low levels. If water is to be removed overhead, it is currently preferred to add water to the reaction mixture after the vent step and prior to the distillation. If a co-solvent is used and the boiling point of the co-solvent is such that co-solvent is also removed during the distillation, it may be necessary to add an amount of co-solvent back to the reaction mixture as well. If this distillation to remove ammonia is conducted in the presence of excess calcium compound, hydrolysis of any residual amide corresponding to the nitrile compound is promoted. The time cycle for this distillation can be set depending on the distillation conditions and the desired level of amide and residual ammonia in the calcium carboxylate product, and will be readily apparent to those of ordinary skill in the art.

After completion of the ammonia removal, it may be necessary to adjust the concentration of the calcium carboxylate product depending on the amount of water (and potentially co-solvent) that has been removed during the distillation to remove ammonia. Concentration adjustment may be needed to ensure that all of the calcium carboxylate is in solution, particularly if the insoluble, excess calcium compound is to be subsequently removed by filtration. In addition, this is the currently preferred point of the process to adjust the concentration if the final product is to be a solution.

After the ammonia removal and concentration adjustment has occurred, the product mixture is neutralized and, optionally, filtered/separated. The neutralization (pH adjustment) and filtration/separation steps can be conducted by any conventional technique known to those of ordinary skill in the art. The specific neutralization and filtration/separation steps utilized will depend on the quality of the starting materials used, impurity levels in the final product, and the desired product quality. Three possible options are described below.

The first option is currently preferred if the highest calcium carboxylate product quality is desired. In this option, the reaction mass is filtered/separated using conventional equipment and techniques after the ammonia removal and concentration adjustment steps to remove excess insoluble calcium compound, as well as any other impurities that may be adsorbed onto the particle surfaces, as well as any other insoluble materials such as insoluble magnesium salts present in the calcium compound used, polymers formed during the reaction, etc. Following the filtration/separation step, the pH is adjusted with carboxylic acid corresponding to the calcium carboxylate to neutralize soluble calcium compound (forming additional calcium carboxylate) and reach the desired pH for the product.

The second option is currently preferred if it is desired to retain the raw material value of the excess calcium compound. In this option, neutralization with carboxylic acid corresponding to the calcium carboxylate to neutralize excess calcium compound present is performed. However, with this option any adsorbed impurities may redissolve in the product. Filtration/separation of the neutralized product is then conducted to remove remaining insolubles.

The third option is feasible if a solid final product is to be produced and the product quality standards are less stringent. In this option, no filtration/separation step is conducted. The product resulting from the ammonia removal and concentration adjustment steps is neutralized with carboxylic acid corresponding to the calcium carboxylate to neutralize excess calcium compound present.

Options one and two are the currently preferred options.

Once any filtration/separation and neutralization operations are conducted, the filtered and neutralized calcium carboxylate product is subjected to final product processing that is dependent on the form of the final product desired, i.e. a solution product or a solid product.

For a solution product, the filtered and neutralized calcium carboxylate product optionally has the concentration adjusted by adding water or calcium carboxylate, and a final filtration using a polishing filter or equivalent separation device may be conducted prior to product storage or packaging.

For a solid product, the filtered and neutralized calcium carboxylate product is recovered and dried. Recovery and drying can be done utilizing any conventional process known to one of ordinary skill in the art. One option is to dry the solution directly to a powder using a spray dryer or by spraying onto dry particles in a fluid bed dryer. A second option is to crystallize the calcium carboxylate product by water evaporation, collection on a filter or centrifuge, and final drying in any conventional solids dryer used to dry wet solids. The first option is currently preferred unless the second option is required by product quality specifications since the second option would require recycle or disposal of a mother liquor stream.

EXAMPLES

Example 1

Propionitrile (22 g; 0.4 mol, supplied by Aldrich Chemical, 97% min), calcium hydroxide (23.2 g, 0.31 mol, supplied by Fisher Scientific, certified grade), and deionized water (81.7 g, 4.54 mol) were charged to a 350 mL, 316 stainless steel autoclave. The autoclave was closed, agitation was initiated, and the unit was pressurized to 106 psig (730.8 KPa) with helium. A helium flow of 30 std $cm^3$/min through the head space was established. The contents of the autoclave were heated with an electric mantel to 161° C. over a period of 0.5 hour. The autoclave temperature was then controlled at 160–161° C. while the autoclave pressure was maintained at 127–142 psig (979 KPa). After 1 hour at 161° C. ammonia was detected in the gas leaving the autoclave with moist pH paper. The heat was turned off after 6.8 hours at which time ammonia was still detectable in the gas leaving the autoclave. The autoclave was cooled overnight and opened the next morning. The autoclave contained a white slurry with a very strong ammonia odor. A sample of the reaction mixture was taken, diluted 1:17.3 with deionized water and analyzed using a Thermo Separation HPLC equipped with a 250×4.60 mm Hypersil 5μ C18-BDS column. The mobile phase consisted of 5% methanol with the balance being 0.2% phosphoric acid in water. A flow rate of 1 mL/min for 12 minutes was used. The calcium propionate and propionamide were quantified with a UV detector operating at 215 λ and propionitrile was quantified with a refractive index detector. The undiluted reactor product was found to contain 24.2% calcium propionate, 114 ppm propionamide, and no detectable propionitrile.

Example 2

Propionitrile (413 g, 7.5 mol, supplied by Solutia Inc., refined: 99.6% min) was charged into a one gallon 316 stainless steel autoclave through a funnel. Calcium hydroxide (305.7 g, 4.13 mol, supplied by Mississippi Lime, CODEX Hydrated Lime), and one-half of the total deionized water charge (total water=1835 g, 101.9 mol) were mixed to produce a slurry which was charged to the autoclave-through the same funnel. The remaining water was used to rinse the calcium hydroxide slurry container and was charged to the autoclave through the funnel. The autoclave was closed and pressurized with nitrogen to 50–60 psig (344.7–413.7 KPa), the pressure relieved, and this step repeated two additional times to purge air from the system. The pressure control valve was set to 150 psig (1034.2 KPa), and a nitrogen flow (200 std $cm^3$/min) through the reactor vapor space was started. The autoclave agitator was started and the contents were heated to 170° C. with a mixture of steam and water under pressure in an internal coil. Once the temperature inside the autoclave reached 170° C., the reaction was allowed to proceed for 12.33 hours after which time the steam was turned off. After the temperature of the autoclave contents dropped to 60° C., the pressure was slowly vented to atmospheric pressure. The product slurry was then drained into a one-gallon bottle (2380.4 grams). The slurry was analyzed by the HPLC method described in Example 1 and was found to contain 31.0% calcium propionate (a quantitative yield within the accuracy of the analysis), 431 ppm propionamide, and no detectable propionitrile.

The product was filtered to remove the insoluble calcium hydroxide to give a filtrate weighing 2211 grams. The bulk of the ammonia was removed on a rotary evaporator under the vacuum provided by a water aspirator and a bath temperature of 60° C. Approximately 400 grams of deionized water was added to the product during the stripping of the ammonia to keep the calcium propionate in solution. To remove the last traces of ammonia and hydrolyze most of the residual propionamide an additional 300 grams of deionized water and 1.0 grams of calcium hydroxide was added. Approximately 300 grams of water and ammonia was removed by atmospheric distillation with a final base temperature of 103° C. Water was added to dissolve all of the calcium propionate. This solution was filtered to obtain 2466 grams of solution containing 29.3% calcium propionate (a quantitative yield within the accuracy of the analysis), 112 ppm of propionamide, and no detectable ammonia. This material was combined with similar material from two additional hydrolysis reactions. The pH of the combined solution was adjusted to 8.1 with propionic acid (supplied by Aldrich, 99% min). Approximately 20% of the water was removed by atmospheric distillation. This produced a slurry from which the bulk of the water was removed on a rotary evaporator. The wet solid was dried in a vacuum oven at 60° C. and 125 mm of Hg for 24 hours to produce a dry white solid. This material assayed as 90.6% calcium propionate, 9.1% water and 200 ppm propionamide.

Example 3

Propionitrile (311.5 g, 5.66 mol, supplied by Solutia Inc., refined: 99.6% min) was charged into a one gallon 316 stainless steel autoclave through a funnel. Calcium hydroxide (229.3 g, 3.09 mol, supplied by Mississippi Lime, CODEX Hydrated Lime), and deionized water (1007.2 g, 55.9 mol) were mixed to produce a slurry and charged to the autoclave through the same funnel. A second portion of deionized water (345.1 g, 19.2 mol) was used to rinse the calcium hydroxide slurry container and was charged to the autoclave through the funnel. The autoclave was pressurized with nitrogen to 45–55 psig (310.3–379.2 KPa), and the pressure relieved to under 25 psig (172.4 KPa). This cycle was repeated two additional times to purge most of the air from the system. The pressure control valve was set to 260 psig (1792.6 KPa), and a nitrogen flow (100 std $cm^3$/min) through the reactor vapor space was started. The autoclave agitator was started and the contents were heated to 200° C. with a mixture of steam and water under pressure in an internal coil. After the autoclave contents had been at 200° C. for one hour, the nitrogen flow was increased to 200 $cm^3$/min to improve the control of the autoclave pressure. After the autoclave contents had been at 200° C. for a total of two hours, the steam was turned off and the reactor pressure was released through a vapor line heated to over 200° C. over a period of 40 minutes. The water and ammonia that flashed from the autoclave was trapped by passing it into a scrubber containing 4862.6 grams of ice water. This scrubber solution weighed 5414.9 grams after all of the autoclave pressure had been released. After the autoclave contents had cooled to less than 60° C. they were drained and weighed (925.1 g). Deionized water (237.2 g) was added to dissolve all of the calcium propionate. This diluted product was analyzed by the HPLC method described in Example 1 and found to contain 28.0% calcium propionate (326 g, 1.75 mol, 62% yield), 119 ppm of propionamide, and no detectable propionitrile. The scrubber solution was found to contain 0.34% calcium propionate and 1.58% ammonia. From the amount of calcium propionate in the scrubber, it was concluded that approximately 66.4 grams of the product was carried into the scrubber by entrainment and that 400 grams of water and 85.5 grams of ammonia were flashed from the autoclave. This represents 90% of the ammonia that would be expected from complete hydrolysis of the propionitrile charged to the autoclave. No attempt was made to quantify the amount of calcium propionate remaining in the reactor after the product was drained.

Example 4

A slurry of calcium hydroxide (23.4 g, 0.316 mol, supplied by Mississippi Lime, CODEX Hydrated Lime) in deionized water (148 g, 8.2 mol) was charge to a 300 mL Hastelloy autoclave which was equipped with a water cooled reflux condenser. The autoclave was pressurized with nitrogen to 235 psig (1620.3 KPa), and the pressure relieved to 10 psig (68.9 KPa). This cycle was repeated two additional times to purge most of the air from the system. The autoclave was then pressurized to 235 psig (1620.3 KPa) and a steady flow of 50 std $cm^3$/min of nitrogen was established across the top of the reflux condenser. After the autoclave contents were heated to 200° C., propionitrile (43.3 mL, 33.8 g, 0.615 mol, supplied by Solutia Inc., refined: 99.6% min) was injected over a period of two hours with a high-pressure syringe pump. The gas leaving the unit was passed through a water scrubber to trap any propionitrile, ammonia, and water escaping the autoclave. Samples of the reactor contents were pulled after the addition of propionitrile was complete, and then one and two hours later. The water in the gas scrubber was also drained, weighed, and replaced with fresh deionized water when each sample was pulled. The reactor contents were analyzed and scrubber samples for propionitrile, propionamide, and calcium propionate by the HPLC method described in Example 1. No calcium propionate or propionamide was found in the scrubber samples indicating that entrainment of the liquid contents of the autoclave into the gas did not occur. The ammonia in the scrubber samples was also determined by titration with 0.1 N HCl. From this data, the following time profile of the weight percent of propionitrile, propionamide and calcium propionate as well as the moles of propionitrile and ammonia leaving the autoclave in the gas were calculated. These results are tabulated below:

| Time (hours) | Propionitrile (weight %) | Propionamide (weight %) | Calcium pionate (weight %) | Propionitrile (mol) | Ammonia (mol) |
|---|---|---|---|---|---|
| 2 | 1.06% | 0.35% | 26.1% | 0.0001 | 0.0012 |
| 3 | 0.00% | 0.13% | 26.9% | 0.0000 | 0.0148 |
| 4 | 0.00% | 0.08% | 27.35% | 0.0000 | 0.0116 |

We claim:

1. A process for producing a calcium carboxylate comprising contacting a nitrile compound, a calcium compound selected from calcium hydroxide, calcium oxide or mixtures thereof, and water at a temperature of about 90° C. to about 250° C. at a sufficient pressure and for a sufficient time to produce a reaction mixture comprising calcium carboxylate.

2. The process of claim 1 wherein said nitrile compound is represented by the formula R—CN wherein R is selected from an aliphatic group, an alicyclic hydrocarbon group, an aromatic hydrocarbon group, or a heterocyclic group, and wherein R is optionally substituted.

3. The process of claim 2 wherein said R is an aliphatic hydrocarbon group.

4. The process of claim 3 wherein said nitrile is propionitrile.

5. The process of claim 1 wherein the molar ratio of calcium compound to nitrile compound is about 0.5:1 to about 0.75:1.

6. The process of claim 5 wherein the molar ratio of calcium compound to nitrile compound is greater than 0.5:1 to about 0.6:1.

7. The process of claim 1 wherein the molar ratio of water to nitrile compound is about 5:1 to about 30:1.

8. The process of claim 7 wherein the molar ratio of water to nitrile compound is about 12:1 to about 15:1.

9. The process of claim 1 further comprising removing ammonia from said reaction mixture.

10. The process of claim 9 further comprising recovering said calcium carboxylate.

11. The process of claim 1 wherein said temperature is about 160° C. to about 220° C.

12. The process of claim 1 further comprising removing ammonia from said reaction mixture, and subsequently recovering the calcium carboxylate.

13. A process for producing a calcium carboxylate comprising
 (a) contacting a nitrile compound, a calcium compound selected from calcium hydroxide, calcium oxide or mixtures thereof, and water in a reaction vessel at a temperature of about 90° C. to about 250° C. at a sufficient pressure and for a sufficient time to produce a first reaction mixture comprising calcium carboxylate, the amide corresponding to said nitrile compound, water and ammonia;
 (b) optionally cooling the first reaction mixture;
 (c) venting the reaction vessel to remove ammonia and produce a second reaction mixture;
 (d) optionally adding additional water to the second reaction mixture;
 (e) heating said second reaction mixture to a suitable temperature to remove additional ammonia and, optionally, water from the second reaction mixture and hydrolyze at least a portion of said amide to produce additional calcium carboxylate; and
 (f) recovering the calcium carboxylate.

14. The process of claim 13 wherein said nitrile compound is represented by the formula R—CN wherein R is selected from an aliphatic group, an alicyclic hydrocarbon group, an aromatic hydrocarbon group, or a heterocyclic group, and wherein R is optionally substituted.

15. The process of claim 14 wherein said R is an aliphatic hydrocarbon group.

16. The process of claim 15 wherein said nitrile is propionitrile.

17. The process of claim 13 wherein the molar ratio of calcium compound to nitrile compound is about 0.5:1 to about 0.75:1.

18. The process of claim 17 wherein the molar ratio of calcium compound to nitrile compound is greater than 0.5:1 to about 0.6:1.

19. The process of claim 13 wherein the molar ratio of water to nitrile compound added in step (a) is about 5:1 to about 30:1.

20. The process of claim 19 wherein the molar ratio of water to nitrile compound added in step (a) is about 12:1 to about 15:1.

21. The process of claim 13 wherein said temperature is about 160° C. to about 220° C.

22. The process of claim 13 wherein said calcium carboxylate is recovered by (i) adjusting the concentration of the product of step (e), (ii) filtering to remove insoluble, unreacted calcium compound, (iii) adding carboxylic acid corresponding to the nitrile compound to neutralize any soluble calcium compound and produce a neutralized product, and (iv) optionally filtering the neutralized product to remove insolubles and produce a neutralized solution product.

23. The process of claim 22 further comprising drying the neutralized solution product to produce solid calcium carboxylate.

24. The process of claim 13 wherein said calcium carboxylate is recovered by (i) adjusting the concentration of the product of step (e), (ii) adding carboxylic acid corresponding to the nitrile compound to neutralize remaining calcium compound and produce a neutralized product, and (iii) optionally filtering the neutralized product to remove insolubles and produce a neutralized solution product.

25. The process of claim 24 further comprising drying the neutralized solution product to produce solid calcium carboxylate.

26. The process of claim 13 wherein said first reaction mixture is cooled prior to said venting in step (c).

27. A process for producing a calcium propionate comprising contacting propionitrile, a calcium compound selected from calcium hydroxide, calcium oxide or mixtures thereof, and water at a temperature of about 90° C. to about 250° C. at a sufficient pressure to achieve the desired temperature and for a sufficient time to produce a reaction mixture comprising calcium propionate;
 wherein the molar ratio of calcium compound to propionitrile is about 0.5:1 to about 0.75:1, and the molar ratio of water to propionitrile is about 5:1 to about 30:1.

28. The process of claim 27 wherein the molar ratio of calcium compound to propionitrile is greater than 0.5:1 to about 0.6:1.

29. The process of claim 27 wherein the molar ratio of water to nitrile compound is about 12:1 to about 15:1.

30. The process of claim 27 wherein said temperature is about 160° C. to about 220° C.

31. The process of claim 27 further comprising removing ammonia from said reaction mixture.

32. The process of claim 31 further comprising recovering said calcium propionate.

33. The process of claim 27 further comprising removing ammonia from said reaction mixture, and subsequently recovering the calcium propionate.

34. A process for producing a calcium propionate comprising (a) contacting a propionitrile, a calcium compound selected from calcium hydroxide, calcium oxide or mixtures thereof, and water in a reaction vessel at a temperature of about 90° C. to about 250° C. at a sufficient pressure and for a sufficient time to produce a first reaction mixture comprising calcium propionate, the propionamide, water and ammonia;

(b) optionally cooling the first reaction mixture;

(c) venting the reaction vessel to remove ammonia and produce a second reaction mixture;

(d) optionally adding additional water to the second reaction mixture;

(e) heating said second reaction mixture to a suitable temperature to remove additional ammonia and, optionally, water from the second reaction mixture and hydrolyze at least a portion of said amide to produce additional calcium propionate; and (f) recovering the calcium propionate wherein the molar ratio of calcium compound to propionitrile is about 0.5:1 to about 0.75:1, and the molar ratio of water to propionitrile is about 5:1 to about 30:1.

35. The process of claim 34 wherein said calcium propionate is recovered by (i) adjusting the concentration of the product of step (e), (ii) filtering to remove insoluble, unreacted calcium compound, (iii) adding a propionic acid to neutralize any soluble calcium compound and produce a neutralized product, and (iv) optionally filtering the neutralized product to remove insolubles and produce a neutralized solution product.

36. The process of claim 35 further comprising drying the neutralized solution product to produce solid calcium propionate.

37. The process of claim 34 wherein said calcium propionate is recovered by (i) adjusting the concentration of the product of step (e), (ii) adding propionic acid to neutralize remaining calcium compound and produce a neutralized product, and (iii) optionally filtering the neutralized product to remove insolubles and produce a neutralized solution product.

38. The process of claim 37 further comprising drying the neutralized solution product to produce solid calcium propionate.

39. The process of claim 34 wherein said temperature is about 160° C. to about 220° C.

40. The process of claim 34 wherein said first reaction mixture is cooled prior to said venting in step (c).

* * * * *

UNITED STATES PATENT AND TRADEMARK OFFICE
CERTIFICATE OF CORRECTION

PATENT NO. : 6,673,964 B1
DATED : January 6, 2004
INVENTOR(S) : Anthony K. Uriarte et al.

It is certified that error appears in the above-identified patent and that said Letters Patent is hereby corrected as shown below:

Column 11,
Line 28, please replace "aliphatic group" with -- aliphatic hydrocarbon group --

Column 12,
Line 9, please replace "aliphatic group" with -- aliphatic hydrocarbon group --

Signed and Sealed this

Twenty-eighth Day of December, 2004

JON W. DUDAS
*Director of the United States Patent and Trademark Office*